US010531916B2

(12) United States Patent
Naka et al.

(10) Patent No.: US 10,531,916 B2
(45) Date of Patent: Jan. 14, 2020

(54) MICROWAVE-IRRADIATING INSTRUMENT

(71) Applicant: MICRON SHIGA INC., Shiga (JP)

(72) Inventors: Shigeyuki Naka, Shiga (JP); Tohru Tani, Shiga (JP)

(73) Assignee: MICRON SHIGA INC., Shiga (JP)

( * ) Notice: Subject to any disclaimer, the term of this patent is extended or adjusted under 35 U.S.C. 154(b) by 495 days.

(21) Appl. No.: 15/114,085

(22) PCT Filed: Nov. 13, 2014

(86) PCT No.: PCT/JP2014/080125
§ 371 (c)(1),
(2) Date: Oct. 18, 2016

(87) PCT Pub. No.: WO2015/072529
PCT Pub. Date: May 21, 2015

(65) Prior Publication Data
US 2017/0020607 A1 Jan. 26, 2017

(30) Foreign Application Priority Data
Nov. 13, 2013 (JP) .................................. 2013-235509

(51) Int. Cl.
*A61B 18/18* (2006.01)
*H05B 6/80* (2006.01)
*A61B 18/00* (2006.01)

(52) U.S. Cl.
CPC ............ *A61B 18/1815* (2013.01); *H05B 6/80* (2013.01); *A61B 2018/00589* (2013.01);
(Continued)

(58) Field of Classification Search
CPC .......... A61B 18/1815; A61B 2018/183; A61B 2018/1412; A61B 2018/00601;
(Continued)

(56) References Cited

U.S. PATENT DOCUMENTS 5,006,825 A * 4/1991 Guilbert ................ H01J 23/005
315/39.53
5,948,009 A * 9/1999 Tu ....................... A61B 18/1485
606/169
(Continued)

FOREIGN PATENT DOCUMENTS

JP 2005312807 A 11/2005
JP 2011135988 A 7/2011
(Continued)

OTHER PUBLICATIONS

International Search Report and Written Opinion issued in corresponding International Patent Application No. PCT/JP2014/080125 dated Dec. 22, 2014 (English translation) (7 pages).
(Continued)

*Primary Examiner* — Eun Hwa Kim
*Assistant Examiner* — Adam Z Minchella
(74) *Attorney, Agent, or Firm* — Kilyk & Bowersox, P.L.L.C.

(57) ABSTRACT

Microwave-irradiating surgical instruments for endoscopic forceps or scope-assisted surgery forceps that have long lead wires often generate heat even during microwave transmission and a water supply device for cooling is necessary. Accordingly, conventional surgical instruments that irradiated energy such as microwaves had a separate passage for passing water (a water supply device) inside the forceps or endoscope. Due to the space occupied by said water supply device, the image cable or work hole diameter could not be enlarged. Moreover, the presence of the water supply device made surgery difficult. The present invention was completed by the discovery that a microwave-irradiating instrument wherein the central conductor is hollow and forms a channel and said channel is used as a water supply tube, etc. solves the above problems without affecting microwave irradiation efficiency.

12 Claims, 7 Drawing Sheets

(52) U.S. Cl.
CPC ............... *A61B 2018/00601* (2013.01); *A61B 2018/00875* (2013.01); *A61B 2018/00982* (2013.01); *A61B 2218/007* (2013.01)

(58) Field of Classification Search
CPC ........... A61B 2018/00589; A61B 2018/00875; A61B 2018/00791; A61B 18/18; A61B 18/14
See application file for complete search history.

(56) References Cited

U.S. PATENT DOCUMENTS

| | | | | |
|---|---|---|---|---|
| 6,652,516 B1* | 11/2003 | Gough | ............... | A61B 18/1477 606/41 |
| 2006/0276780 A1* | 12/2006 | Brace | .................... | A61B 18/18 606/33 |
| 2008/0065059 A1* | 3/2008 | Lukowiak | ............... | A61B 18/18 606/33 |
| 2008/0147056 A1* | 6/2008 | van der Weide | ...... | A61B 18/18 606/33 |
| 2010/0030107 A1* | 2/2010 | Hancock | ............ | A61B 10/0233 600/567 |
| 2010/0053015 A1* | 3/2010 | Willyard | ................ | A61B 18/18 343/790 |
| 2010/0057078 A1* | 3/2010 | Arts | ........................ | A61B 10/06 606/41 |
| 2010/0286686 A1* | 11/2010 | Hancock | ................ | A61B 18/18 606/33 |
| 2011/0166564 A1* | 7/2011 | Merrick | ............. | A61B 17/0401 606/33 |
| 2011/0213352 A1* | 9/2011 | Lee | .................... | A61B 18/1815 606/33 |
| 2012/0053577 A1* | 3/2012 | Lee | .................... | A61B 18/1815 606/33 |
| 2012/0123409 A1 | 5/2012 | Tani et al. | | |
| 2013/0144284 A1* | 6/2013 | Behnke, II | ......... | A61B 18/1815 606/33 |
| 2013/0165915 A1* | 6/2013 | Thiel | ...................... | A61B 90/57 606/33 |
| 2013/0178842 A1* | 7/2013 | Reid, Jr. | ............ | A61B 18/1477 606/33 |
| 2013/0289557 A1* | 10/2013 | Hancock | ............ | A61B 18/1815 606/33 |
| 2013/0324910 A1* | 12/2013 | Ohri | ................... | A61B 10/0233 604/21 |

FOREIGN PATENT DOCUMENTS

| | | |
|---|---|---|
| WO | 2008044013 A2 | 4/2008 |
| WO | 2012095653 A1 | 7/2012 |

OTHER PUBLICATIONS

Office Action issued in corresponding Japanese Patent Application No. 2015-547795—English translation (2 pages).
Office Action issued in corresponding Japanese Patent Application No. 2015-547795 dated Jun. 24, 2016—English translation (2 pages).

* cited by examiner (a) (b) (c)

(a) (b)

MICROWAVE-IRRADIATING INSTRUMENT

TECHNICAL FIELD

The present invention relates to a microwave-irradiating instrument, more particularly, to a medical microwave-irradiating instrument, and more specifically, to a medical microwave-irradiating instrument including a central conductor having a channel.

The present application is a National Stage Application of PCT/JP2014/080125, filed Nov. 13, 2014, which claims priority from Japanese Patent Application No. 2013-235509, the disclosure of which is incorporated herein by reference.

BACKGROUND ART

There has been known that a microwave can coagulate (immobilize) body tissues such as digestive organs, a liver, a bladder, a prostate, a uterus, blood vessels, and intestinal tracts at low temperature. Then, various devices for assisting surgery through use of the microwave have been developed.

In Patent Literature 1, there is disclosed a microwave-irradiating apparatus including a probe having an elongated shaft (14). The shaft includes a tubular outer peripheral wall (18), a radiation part (15) arranged at a tip end of the shaft (14), a transmission line (17) extending to the radiation part in the tubular outer peripheral wall (18), and an elongated branching member (19) extending together with the transmission line (17) in a vertical direction of the shaft (14). A side wall of the transmission line (17) and a side wall of the branching member (19) are held in contact with each other and held in contact with an inner surface of the tubular outer peripheral wall (18) at two separate different positions, to thereby provide a pair of liquid current passages (20, 21) in the shaft (14). At a time of use, a cooling liquid flows down through one of the passages (20) and returns through the other passage (21).

In Patent Literature 2, there is disclosed a microwave-irradiating apparatus including a hollow electrode capable of supplying a medicine to a microwave-irradiating part.

However, in any of the patent literatures of the related art, there are neither disclosed nor suggested a microwave-irradiating instrument including a central conductor forming a channel, the instrument having a coaxial cable shape, and further the instrument serving as forceps, scissors, or a knife according to the present invention.

CITATION LIST

Patent Literature

[PTL 1] JP 2011-511424 A
[PTL 2] U.S. Pat. No. 5,599,294 B2

SUMMARY OF INVENTION

Technical Problem

During current endoscopic surgery and open surgery, a tissue is subjected to coagulation, hemostasis, and cutting through use of an ultrasonic irradiation surgery instrument, a high-frequency irradiation surgery instrument, or a microwave-irradiating surgery instrument. Further, the tissue is washed with saline or the like and sucked simultaneously with those operations. With this, a surgical field is observed well, and adhesion of the tissue to the instruments is prevented. Further, efficient irradiation of energy such as a microwave to the tissue is achieved.

Further, a microwave-irradiating surgery instrument for endoscopic forceps or scope-assisted surgery forceps having a long conductive wire often generates heat even during microwave transmission, and hence requires a water supply device for cooling.

In view of this, in a related-art energy-irradiating surgery instrument that radiates a microwave or the like, a passage configured to allow water to pass therethrough (water supply device) is separately installed in the forceps or an endoscope. Due to the presence of a space for the water supply device, an image cable and a hole diameter for an operation cannot be enlarged. Further, the presence of the water supply device causes difficulty in surgery.

Solution to Problem

The inventors of the present invention have repeatedly conducted extensive investigations to solve the above-mentioned problem. As a result, the inventors of the present invention have found that a microwave-irradiating instrument, in which a central conductor is formed into a hollow shape to form a channel, and the channel is used as a water supply tube or the like, can transmit a microwave with a surface effect, and can solve the above-mentioned problems without influencing the microwave irradiation efficiency. Thus, the present invention has been achieved.

That is, the present invention includes the following aspects.

1. A microwave-irradiating instrument, including:
   (1) a central conductor having a hollow shape;
   (2) a channel formed of the hollow shape;
   (3) an external conductor configured to directly or indirectly cover a part or an entirety of the central conductor;
   (4) a microwave-irradiating part or a microwave-receiving part directly or indirectly connected to the central conductor; and
   (5) a microwave-receiving part or a microwave-irradiating part directly or indirectly connected to the external conductor,
   in which the channel includes forceps, a knife, scissors, a transmission cable, an energy conductive wire and/or instrument, a sensor, and/or a vibration function instrument.

2. A microwave-irradiating instrument according to Item 1, including:
   (1) a central conductor having a hollow shape;
   (2) a channel formed of the hollow shape;
   (3) an insulator configured to cover a part or an entirety of the central conductor;
   (4) an external conductor configured to cover apart or an entirety of the insulator;
   (5) a microwave-irradiating part or a microwave-receiving part directly or indirectly connected to the central conductor; and
   (6) a microwave-receiving part or a microwave-irradiating part directly or indirectly connected to the external conductor,
   in which the channel includes forceps, a knife, scissors, a transmission cable, an energy conductive wire and/or instrument, a sensor, and/or a vibration function instrument.

3. A microwave-irradiating instrument according to Item 1 or 2, in which the channel includes endoscopic forceps or scope-assisted surgery forceps to enable resection of a microwave irradiation target.

4. A microwave-irradiating instrument according to any one of Items 1 to 3, in which two blades of the forceps or two blades of the scissors respectively serve as the microwave-irradiating part and the microwave-receiving part, and in which the two blades are capable of applying and receiving a microwave.

5. A microwave-irradiating instrument according to any one of Items 1 to 3, in which the microwave-irradiating part is located at a tip end of the central conductor and has a shape of the blade for the forceps or a shape of the blade for the scissors, in which the microwave-receiving part is located at a tip end of the external conductor and has the shape of the blade for the forceps or the shape of the blade for the scissors, and in which the two blades are capable of applying and receiving a microwave.

6. A microwave-irradiating instrument according to Item 1 or 2, in which the channel includes an endoscopic knife or a scope-assisted surgery knife to enable resection of a microwave irradiation target.

7. A microwave-irradiating instrument according to any one of Items 1 to 3 and 6, in which the knife serves as the microwave-receiving part.

8. A microwave-irradiating instrument according to any one of Items 1 to 3 and 6, in which the microwave-receiving part is located at a tip end of the external conductor and has a shape of the knife.

9. A microwave-irradiating instrument according to any one of Items 1 to 8, in which the channel includes a connector for connection to a microwave oscillator and a suction tube, and in which the channel is capable of simultaneously performing a function of transmitting a microwave and functions of the suction tube and a supply tube through the connector.

10. A microwave-irradiating instrument according to Item 1 or 2, in which the channel comprises a supply tube and/or a suction tube, and in which the channel enables a liquid and/or air to pass through the channel.

11. A microwave-irradiating instrument according to Item 1 or 2, in which the channel includes a transmission cable including a camera at a tip end of the transmission cable to enable acquisition of an image of a microwave irradiation target.

12. A microwave-irradiating instrument according to Item 1 or 2, in which the channel includes an energy supply conductive wire and/or instrument configured to supply energy other than a microwave to enable irradiation of the energy other than the microwave to a microwave irradiation target.

13. A microwave-irradiating instrument according to Item 12, in which the energy supply conductive wire and/or instrument has a hollow structure.

14. A microwave-irradiating instrument according to Item 1 or 2, in which the channel includes a temperature and/or electric resistance measurement sensor to enable measurement of a temperature and/or an electric resistance value of a microwave irradiation target.

15. A microwave-irradiating instrument according to Item 1 or 2, in which the channel includes the vibration function instrument to enable vibration of a microwave irradiation target.

16. A microwave-irradiating instrument according to any one of Items 1 to 15, in which the central conductor occupies a part of the channel.

17. A microwave-irradiating instrument according to any one of Items 1 to 16, in which the microwave-irradiating instrument comprises a coaxial cable.

18. A microwave-irradiating instrument according to any one of Items 1 to 16, in which the microwave-irradiating instrument comprises a coaxial cable-shaped microwave transmission instrument.

19. A microwave-irradiating instrument according to any one of Items 1 to 18, in which the microwave-irradiating instrument comprises a medical microwave-irradiating instrument.

20. A microwave-irradiating instrument according to any one of Items 1 to 19, in which a combination of the microwave-irradiating part and the micro-wave receiving part is any one of the combinations comprising:

(1) the microwave-irradiating part or the microwave-receiving part directly or indirectly connected to the central conductor includes a brush-like structure, and the microwave-receiving part or the microwave-irradiating part directly or indirectly connected to the external conductor includes a brush-like structure;

(2) the microwave-irradiating part or the microwave-receiving part directly or indirectly connected to the central conductor includes a brush-like structure, and the microwave-receiving part or the microwave-irradiating part directly or indirectly connected to the external conductor is located at the tip end of the external conductor;

(3) the microwave-irradiating part or the microwave-receiving part directly or indirectly connected to the central conductor is located at the tip end of the central conductor, and the microwave-receiving part or the microwave-irradiating part directly or indirectly connected to the external conductor includes a brush-like structure;

(4) the microwave-irradiating part or the microwave-receiving part directly or indirectly connected to the central conductor is located at the tip end of the central conductor, and the microwave-receiving part or the microwave-irradiating part directly or indirectly connected to the external conductor is located at the tip end of the external conductor;

(5) the microwave-irradiating part or the microwave-receiving part directly or indirectly connected to the central conductor is located at the tip end of the central conductor and has a tapered shape or a needle-like shape, and the microwave-receiving part or the microwave-irradiating part directly or indirectly connected to the external conductor is located at the tip end of the external conductor and has a tapered shape or a needle-like shape;

(6) the microwave-irradiating part or the microwave-receiving part directly or indirectly connected to the central conductor includes an electrode, and the microwave-receiving part or the microwave-irradiating part directly or indirectly connected to the external conductor includes an electrode;

(7) the microwave-irradiating part or the microwave-receiving part directly or indirectly connected to the central conductor, and the microwave-receiving part or the microwave-irradiating part directly or indirectly connected to the external conductor, form a ring through intermediation of an insulator;

(8) the microwave-irradiating part or the microwave-receiving part directly or indirectly connected to the central conductor includes the forceps or the scissors, and the microwave-receiving part or the microwave-irradiating part directly or indirectly connected to the external conductor includes the forceps or the scissors; and (9) the microwave-irradiating part or the microwave-receiving part directly or indirectly connected to the central conductor includes the knife, or the microwave-receiving part or the microwave-irradiating part directly or indirectly connected to the external conductor includes the knife.

21. A microwave-irradiating instrument according to any one of Items 1 to 19, in which a combination of the microwave-irradiating part and the microwave receiving part is any one of the combinations comprising:

(1) the microwave-irradiating part directly or indirectly connected to the central conductor includes a brush-like structure, and the microwave-receiving part directly or indirectly connected to the external conductor includes a brush-like structure;

(2) the microwave-irradiating part directly or indirectly connected to the central conductor is located at the tip end of the central conductor, and the microwave-receiving part directly or indirectly connected to the external conductor is located at the tip end of the external conductor; and (3) the microwave-irradiating part directly or indirectly connected to the central conductor includes a brush-like structure, and the microwave-receiving part directly or indirectly connected to the external conductor is located at the tip end of the external conductor.

Advantageous Effects of Invention

As compared to the related-art microwave-irradiating surgery instrument, the microwave-irradiating instrument of the present invention, in particular, the medical microwave-irradiating instrument has succeeded in extreme reduction in size, and in addition, can easily perform coagulation, hemostasis, washing, and suction of a tissue, and efficiently perform those operations within a short period of time.

Further, the microwave-irradiating instrument of the present invention is not limited to medical use and is applicable to industrial use.

BRIEF DESCRIPTION OF DRAWINGS

FIG. 4(b) is an illustration of microwave irradiation results obtained by using the microwave-irradiating instrument according to the second embodiment.

DESCRIPTION OF EMBODIMENTS

Figure 1:
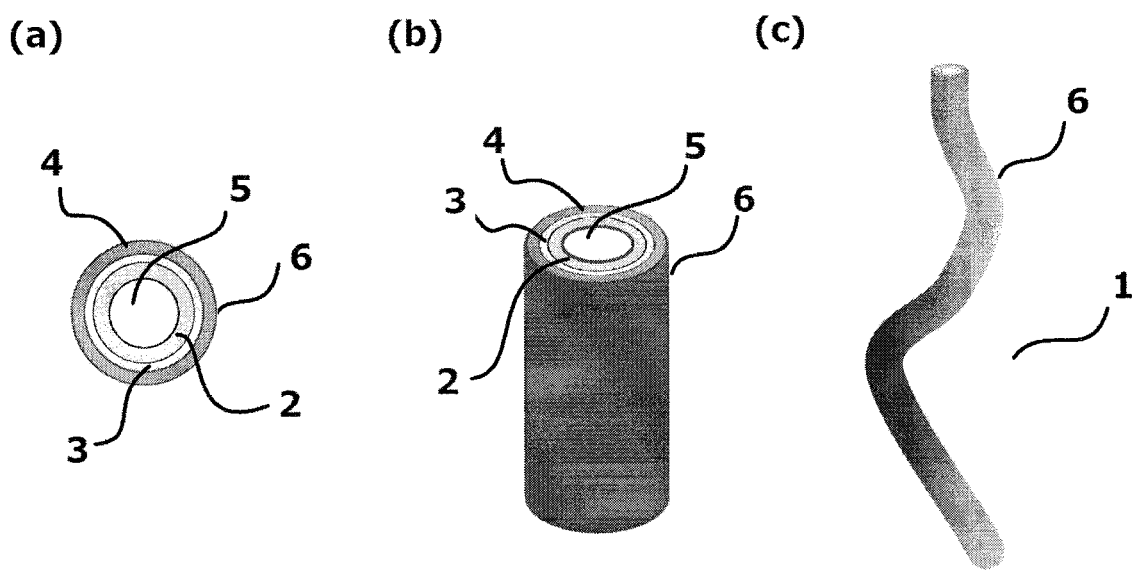
FIG. 1(a) is a sectional view of a tip end of a microwave-irradiating instrument including a channel.
FIG. 1(b) is a side view of the microwave-irradiating instrument including the channel.
FIG. 1(c) is a view of a soft coaxial cable (microwave-irradiating instrument including the channel).

Hereinafter, the present invention is described with reference to the drawings. However, the present invention is not limited to microwave-irradiating instruments illustrated in the drawings.

A microwave-irradiating instrument of the present invention, in particular, a medical microwave-irradiating instrument includes:

(1) a central conductor having a hollow shape;

(2) a channel formed of the hollow shape (hollow structure);

(3) an external conductor configured to directly or indirectly cover a part or an entirety of the central conductor;

(4) a microwave-irradiating part or a microwave-receiving part directly or indirectly connected to the central conductor; and (5) a microwave-receiving part or a microwave-irradiating part directly or indirectly connected to the external conductor.

More specifically, the microwave-irradiating instrument includes:

(1) a central conductor having a hollow shape;

(2) a channel formed of the hollow shape (hollow structure);

(3) an insulator configured to cover a part or an entirety of the central conductor;

(4) an external conductor configured to cover a part or an entirety of the insulator;

(5) a microwave-irradiating part or a microwave-receiving part directly or indirectly connected to the central conductor; and (6) a microwave-receiving part or a microwave-irradiating part directly or indirectly connected to the external conductor.

It is preferred that the channel include forceps, a knife, scissors, a transmission cable, an energy conductive wire and/or instrument, a sensor, and/or a vibration function instrument.

It is preferred that the microwave-irradiating instrument of the present invention include a coaxial cable.

Further, it is preferred that the microwave-irradiating instrument of the present invention include a coaxial cable-shaped microwave transmission instrument.

(Channel)

A central conductor 2 of a microwave-irradiating instrument 1 of the present invention has a feature in that a channel 5 is formed of a hollow shape. In the microwave-irradiating instrument 1 including the central conductor 2 that includes the channel 5, the presence of the channel 5 does not substantially influence the microwave irradiation efficiency.

In addition, the central conductor 2 may occupy a part of the channel 5.

Further, as a material for the central conductor 2 of the present invention, there are exemplified copper, bronze, aluminum, and the like, and the channel 5 can be formed by a method known per se. For example, the channel 5 can be formed by hollowing out an inside of phosphor bronze having a cylindrical shape.

In addition, the central conductor 2 including the channel 5 can be formed by winding a phosphor bronze wire or the like around a pipe of the like made of a stainless steel material having a cylindrical shape or the like. Further, the central conductor 2 including the channel 5 can be formed by plating with phosphor bronze a pipe or the like made of a stainless steel material having a cylindrical shape or the like.

The central conductor 2 including such channel 5 has a feature in that a diameter of the central conductor 2 can be reduced remarkably.

Further, a small hole 16 and/or a slit can be formed in the channel. Through the small hole and/or the slit, water, therapeutic agents, and the like can be supplied to a microwave irradiation target tissue. Further, blood, a body fluid, and the like can be sucked therefrom, as described below.

(Application of Channel)

The channel 5 of the present invention can have any one of the following functions, but there is no particular limitation on the functions of the channel 5.

(1) Supply Tube

When a pump 14 known per se is connected to an end 7 (see FIG. 2) of a coaxial cable, water, therapeutic agents, and the like can be supplied to a microwave irradiation target tissue through the channel 5.

For example, when a microwave is radiated from an elongated conductive wire such as a soft endoscope, a microwave-irradiating instrument generates heat. However, the instrument can be cooled by refluxing water through the channel serving as a supply tube.

(2) Suction Tube

When a suction device 13 known per se is connected to the end 7 (see FIG. 2) of the coaxial cable, blood, a body fluid, and the like in a microwave irradiation region can be sucked through the channel 5.

(3) Introduction Tube for Sensor

When a temperature sensor known per se or the like is introduced into the channel 5 (see FIG. 2), temperature of a microwave irradiation target can be measured easily.

(4) Introduction Tube for Vibration Function Device

When a vibration function device known per se is introduced into the channel 5 (see FIG. 2), the microwave irradiation target can be vibrated easily.

(5) Double Tube Serving as Supply Tube and Suction Tube

Figure 5:
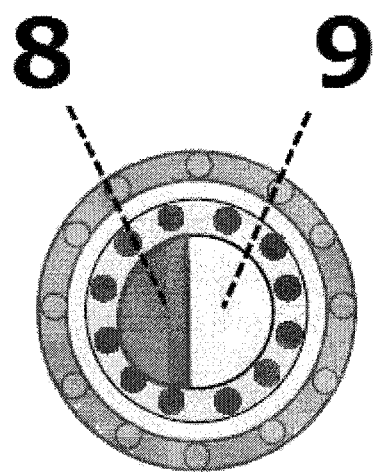
FIG. 5 is a sectional view of a tip end of the microwave-irradiating instrument including the channel serving as a supply tube and a suction tube.

When the suction device 13 known per se and/or the pump 14 known per se are connected to the end 7 of the coaxial cable, water, therapeutic agents, and the like can be supplied to the microwave irradiation target tissue through the channel 5, and simultaneously, blood, a body fluid, and the like can be sucked therefrom through the channel 5. Further, by partitioning a space for the channel 5 into two regions, there can be arranged two tubes, that is, a supply tube 9 and a suction tube 8 (see FIG. 5).

(6) Introduction Tube for Transmission Cable

When a transmission cable known per se is introduced into the channel 5 (see FIG. 2), signal information of the microwave irradiation target can be acquired easily.

For example, when a transmission cable including a camera known per se at a tip end is introduced into the channel 5 (see FIG. 2), an image of the microwave irradiation target can be acquired easily.

(7) Introduction Tube for Energy Supply Device (Energy Conductive Wire and/or Instrument)

When an energy supply device configured to supply light, a direct current, an alternating current, an ultrasonic wave, a high-frequency wave, or the like is introduced into the channel 5 (see FIG. 2), the energy can be supplied to the microwave irradiation target easily.

For example, a direct current is supplied to the microwave irradiation target, and further, a change in a direct current electric resistance value (preferably, the direct current electric resistance value reaches 0) is measured. Thus, the completion of coagulation of a tissue can be detected.

In addition to the irradiation of a microwave, the following energy can also be used at the same time.

Hemostasis auxiliary enhancement can be performed by supplying a high-frequency wave to the microwave irradiation target.

A tissue can be burnt out by supplying an ultrasonic wave to the microwave irradiation target.

When light is supplied to the microwave irradiation target, a surgical field can be illuminated.

In addition, the energy conductive wire and/or instrument may have a hollow structure, and a sensor and the like may be introduced into the hollow structure.

Figure 7:
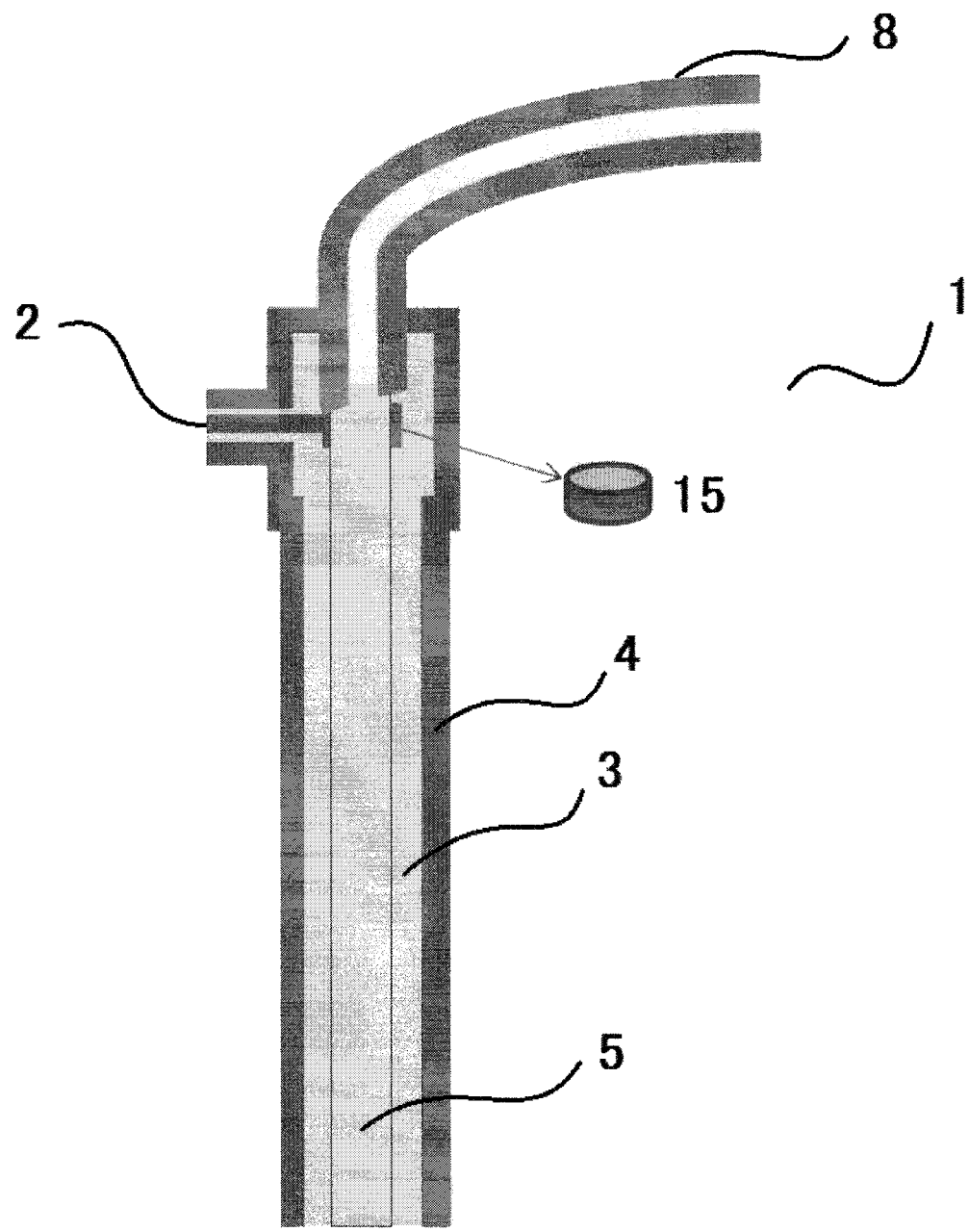
FIG. 7 is a sectional view of the microwave-irradiating instrument in which the channel contains a connector.

Further, as illustrated in FIG. 7, the channel 5 includes the connector 15 for connection to a microwave oscillator and the suction tube 8. Through the connector 15, the channel 5 can simultaneously perform a function of transmitting a microwave and each function (in particular, functions of the supply tube and the suction tube) described in the paragraphs above.

(Central Conductor, External Conductor)

There is no particular limitation on shapes of the central conductor 2, an insulator 3, and an external conductor 4 of the microwave-irradiating instrument 1 of the present invention. The central conductor 2, the insulator 3, and the external conductor 4 may have a cylindrical shape or a square pole shape, and are preferred to form a coaxial cable 6 having a coaxial form (see FIG. 1).

The tip end (microwave irradiation direction) of the central conductor 2 is directly or indirectly connected to a microwave-irradiating part 10 or a microwave-receiving part 11. The tip end of the central conductor 2 itself may serve as the microwave-irradiating part 10 or the microwave-receiving part 11.

The tip end (microwave irradiation direction) of the external conductor 4 is directly or indirectly connected to the microwave-receiving part 11 or the microwave-irradiating part 10. The tip end of the external conductor 4 itself may serve as the microwave-receiving part 11 or the microwave-irradiating part 10.

The microwave-irradiating part 10 refers to an electrode configured to supply a microwave to an irradiation target, and the microwave-receiving part 11 refers to a GND electrode for return of the microwave. Through supply of a microwave from the end (opposite to the microwave irradiation direction) of the central conductor 2 or the end (opposite to the microwave irradiation direction) of the external conductor 4, the microwave can be radiated from the tip end of the central conductor 2 or the external conductor 4.

(Coaxial Cable)

The microwave-irradiating instrument 1 of the present invention can be inserted into an endoscope and/or a catheter by setting the coaxial cable 6 (see FIG. 1(c)) used in the present invention to be soft. During open surgery such as laparotomy, it is preferred that the microwave-irradiating instrument 1 include a gripping portion formed of an insulator, which is to be gripped by an operator.

Further, the coaxial cable 6 used in the present invention includes, for example, the central conductor 2 of a conductive body made of phosphor bronze, a shield tube of the insulator 3 (made of, for example, Teflon (trademark) or ceramics) configured to cover the central conductor 2, and an earth pipe of the external conductor 4 (conductive body) made of brass or the like. The outer side of the coaxial cable may be covered with a shield holder (also called "guide tube"). It is preferred that the shield holder be formed of a nonconductive member (for example, a nonmagnetic coil of Teflon (trademark), fluoloresin, or ceramics).

The central conductor 2 of the present invention is formed into a hollow shape to form the channel 5, and the channel 5 is used as the supply tube 9, the suction tube 8, and the like, to thereby save the space for a supply device and a suction device. With this, the diameter of the coaxial cable 6 can be reduced.

Further, the diameter of the coaxial cable 6 including the central conductor 2 that includes the channel 5 as described above (formed by winding a phosphor bronze wire or the like around a pipe or the like made of a stainless steel material having a cylindrical shape or the like, or formed by plating a pipe or the like made of a stainless steel material having a cylindrical shape or the like with phosphor bronze) can be reduced by about 30% or more as compared to the diameter of a known coaxial cable having the same function. That is, the capacity of the microwave-irradiating instrument having a coaxial cable shape of the present invention can be reduced by from about 10% to about 90% as compared to the capacity of the known coaxial cable having the same function.

(Shape of Coaxial Cable)

Figure 6:
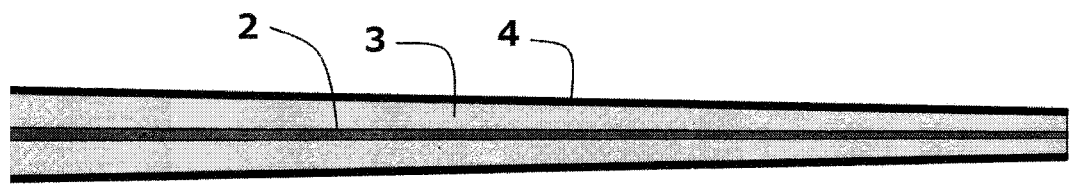
FIG. 6 is a sectional view of a tapered coaxial body.

It is preferred that the coaxial cable 6 be formed into a tapered coaxial body (hereinafter sometimes referred to as "tapered coaxial body") by setting the ratio between the sectional area (preferably, the diameter) of the central conductor 2 and the sectional area (preferably, the inner diameter) of the external conductor 4 to be constant, and reducing the sectional area (diameter) of the central conductor 2 and the sectional area (inner diameter) of the external conductor 4 gradually or stepwisely (see FIG. 6).

Specifically, it is preferred that the ratio between the diameter of the tip end of the central conductor 2 and the diameter of the end of the central conductor 2, and the ratio between the inner diameter of the tip end of the external conductor 4 and the inner diameter of the end of the external conductor maintain substantially the same ratio, and that the central conductor 2 and the external conductor 4 be reduced toward the tip ends gradually or stepwisely.

Such tapered coaxial body has remarkably high microwave irradiation efficiency.

(Irradiation Microwave)

The irradiation microwave of the microwave-irradiating instrument 1 of the present invention is not particularly limited, but falls within a range of from 300 MHz to 300 GHz, preferably a range of from 3 GHz to 30 GHz. The microwave irradiation method of the microwave-irradiating instrument 1 of the present invention is not particularly limited, and can easily be achieved by connecting the coaxial cable 6 directly or indirectly (through a separate coaxial cable) to a microwave oscillator known per se that generates a microwave or by incorporating the oscillator into the microwave-irradiating instrument 1.

The microwave irradiation device to be used in the present invention enables treatment with small electric power and is also excellent in safety. The electric power to be used in the present invention falls within a range of from 0.1 W to 100 W, preferably a range of from 0.5 W to 60 W, more preferably a range of from 1 W to 40 W.

(Combination of Microwave-irradiating Part and Microwave-receiving Part)

Combinations of the microwave-irradiating part 10 and the microwave-receiving part 11 of the microwave-irradiating instrument 1 (in particular, the medical microwave-irradiating instrument 1) of the present invention are as described below but are not particularly limited.

(1) The microwave-irradiating part 10 or the microwave-receiving part 11 directly or indirectly connected to the central conductor 2 includes a brush-like structure 12, and the microwave-receiving part 11 or the microwave-irradiating part 10 directly or indirectly connected to the external conductor 4 includes the brush-like structure 12.

(2) The microwave-irradiating part 10 or the microwave-receiving part 11 directly or indirectly connected to the central conductor 2 includes the brush-like structure 12, and the microwave-receiving part 11 or the microwave-irradiating part 10 directly or indirectly connected to the external conductor 4 is located at the tip end of the external conductor 4.

(3) The microwave-irradiating part 10 or the microwave-receiving part 11 directly or indirectly connected to the central conductor 2 is located at the tip end of the central conductor 2, and the microwave-receiving part 11 or the microwave-irradiating part 10 directly or indirectly connected to the external conductor 4 includes the brush-like structure 12.

(4) The microwave-irradiating part 10 or the microwave-receiving part 11 directly or indirectly connected to the central conductor 2 is located at the tip end of the central conductor 2, and the microwave-receiving part 11 or the microwave-irradiating part 10 directly or indirectly connected to the external conductor 4 is located at the tip end of the external conductor 4.

(5) The microwave-irradiating part 10 or the microwave-receiving part 11 directly or indirectly connected to the central conductor 2 includes an electrode, and the microwave-receiving part 11 or the microwave-irradiating part 10 directly or indirectly connected to the external conductor 4 includes an electrode.

(6) The microwave-irradiating part 10 or the microwave-receiving part 11 directly or indirectly connected to the central conductor 2 and the microwave-receiving part 11 or the microwave-irradiating part 10 directly or indirectly connected to the external conductor 4 form a ring through intermediation of an insulator.

A root portion of a polyp-shaped living tissue can be subjected to hemostasis, coagulation, immobilization, and/or sealing with the ring structure.

(7) The microwave-irradiating part 10 or the microwave-receiving part 11 directly or indirectly connected to the central conductor 2 includes the forceps or the scissors, and the microwave-receiving part 11 or the microwave-irradiating part 10 directly or indirectly connected to the external conductor 4 includes the forceps or the scissors.

(8) The microwave-irradiating part 10 or the microwave-receiving part 11 directly or indirectly connected to the central conductor 2 is located at the tip end of the central conductor 2 and has a tapered shape or a needle-like shape, and the microwave-receiving part 11 or the microwave-irradiating part 10 directly or indirectly connected to the external conductor 4 is located at the tip end of the external conductor 4 and has a tapered shape or a needle-like shape.

(9) The microwave-irradiating part 10 or the microwave-receiving part 11 directly or indirectly connected to the central conductor 2 includes the knife, or the microwave-receiving part 11 or the microwave-irradiating part 10 directly or indirectly connected to the external conductor 4 includes the knife.

The preferable combinations of the microwave-irradiating part 10 and the microwave-receiving part 11 of the microwave-irradiating instrument 1 (in particular, the medical microwave-irradiating instrument 1) of the present invention are described below.

(1) The microwave-irradiating part 10 directly or indirectly connected to the central conductor 2 includes the brush-like structure 12, and the microwave-receiving part 11 directly or indirectly connected to the external conductor 4 includes the brush-like structure 12 (see FIG. 3(b)).

(2) The microwave-irradiating part 10 directly or indirectly connected to the central conductor 2 is located at the tip end of the central conductor 2, and the microwave-receiving part 11 directly or indirectly connected to the external conductor 4 is located at the tip end of the external conductor 4 (see FIG. 3(a)).

(3) The microwave-irradiating part 10 directly or indirectly connected to the central conductor 2 includes the brush-like structure 12, and the microwave-receiving part 11 directly or indirectly connected to the external conductor 4 is located at the tip end of the external conductor 4 (see FIG. 3(c)).

(Brush-like Structure)

Figure 2:
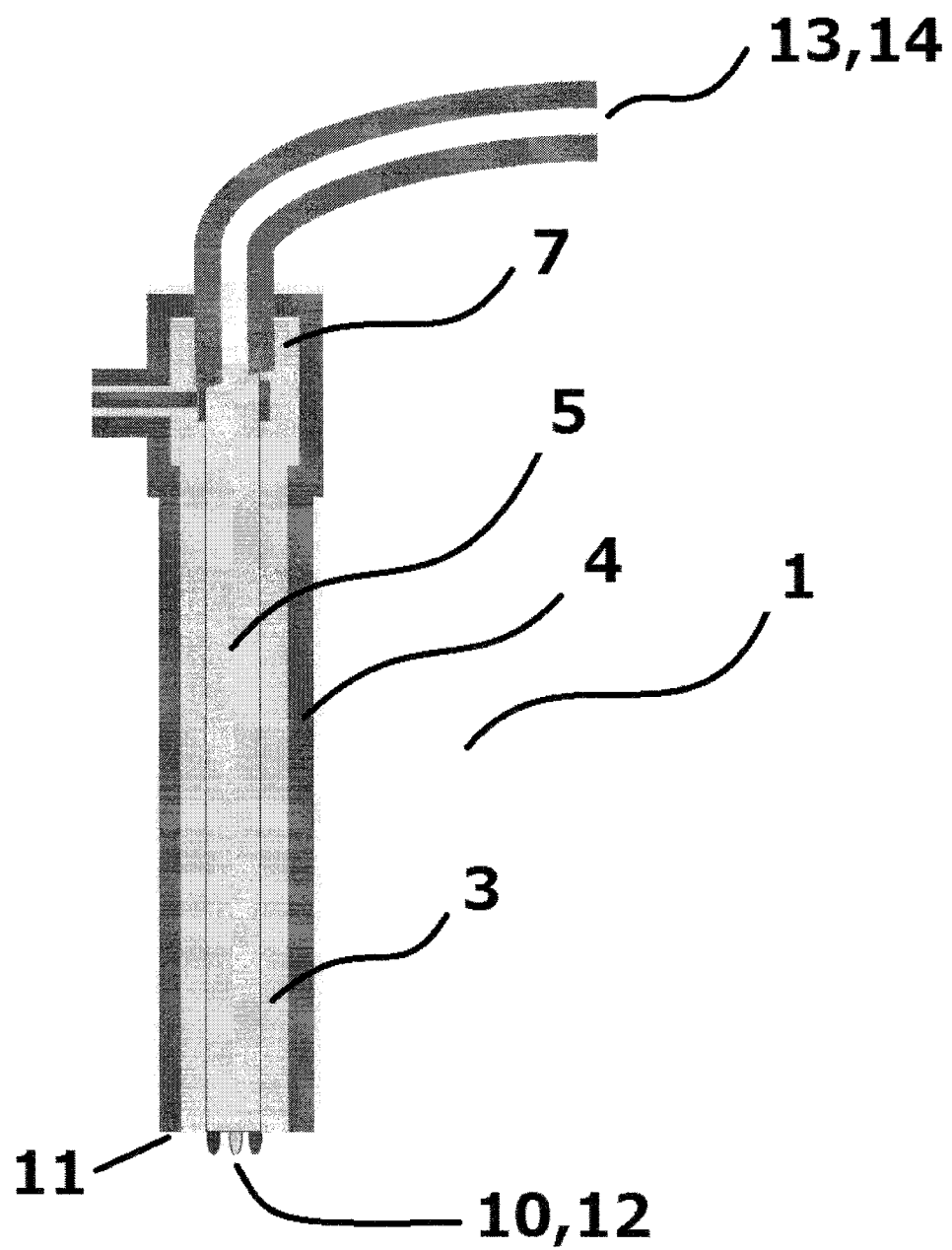
FIG. 2 is a sectional view of the microwave-irradiating instrument including the channel.

The brush-like structure 12 of the present invention is a brush-like portion for scraping off an organ (applying a pressure to living tissue), which is brought into contact with the organ (see "12" in FIG. 2).

Further, the brush-like structure 12 of the present invention is not particularly limited as long as the brush-like structure 12 is made of a material that has stiffness and elasticity capable of scraping off an organ and that is capable of being the microwave irradiation part 10 and/or the microwave receiving part 11. For example, a wide variety of conductive materials such as iron, copper, titanium, stainless steel, phosphor bronze, or brass can be used. Phosphor bronze, stainless steel, brass, and the like are preferably exemplified.

A length of each brush piece of the brush-like structure 12 falls within a range of from 0.5 mm to 25 mm, a range of from 1 mm to 20 mm, or a range of from 5 mm to 15 mm. An optimum length for stiffness and elasticity in accordance with the hardness of each organ to be required for scraping off an organ (in particular, a solid organ) is selected appropriately. When the brush-like structure 12 is extremely short, the brush-like structure 12 has a protrusion shape.

The brush-like structure 12 includes several pieces or tens of pieces in each unit, and the units are ideally converged in a line. However, the pieces may spread from about 5.0 mm to about 7.0 mm in a longitudinal direction and from about 2.0 mm to about 6.0 mm in a lateral direction. As the total lateral width of the brush-like structure 12, the range of from 0.2 mm to 3 cm, from 0.5 mm to 2.0 cm, from 0.6 mm to 1.5 cm, or from 0.7 mm to 11 mm is exemplified. The units may or may not be held in contact with each other.

Although the diameter of one piece of the brush-like structure 12 falls within a range of from 0.1 mm to 0.5 mm, a range of from 0.2 mm to 0.5 mm, or a range of from 0.3 mm to 0.5 mm, the optimum diameter for stiffness and elasticity in accordance with the hardness of each organ to be required for scraping off a solid organ is selected appropriately.

The brush-like structure 12 may be made of a plurality of metallic needles or may have a wire shape. Further, the brush-like structure 12 may be branched off from the central conductor 2 or the external conductor 4 to extend to form a brush shape.

The brush-like structure 12 may include one or a plurality of rows of a transverse brush, a random arrangement brush, one or a plurality of rows of a circular arrangement brush, or one or a plurality of rows of a semi-circular arrangement brush.

One row of a transverse brush refers to a brush in which brush pieces are arranged laterally in a row so as to have a comb-like shape.

A plurality of rows of a transverse brush refers to a brush in which brush pieces are arranged laterally in a plurality of rows so as to have a shape in which a plurality of combs are arranged. In the case of two rows of a transverse brush, one row can be used as the microwave irradiation part 10, and another row can be used as the microwave receiving part 11. As a matter of course, all the rows can also be used as the microwave irradiation part 10 or the microwave receiving part 11. Further, in the case of a plurality of rows of a transverse brush, the respective rows can be used as the microwave irradiation part 10 and the microwave receiving part 11 alternately. Alternatively, one or a plurality of rows of a transverse brush, in which each brush piece is used as the microwave irradiation part 10 and the microwave receiving part 11, can also be used.

The random arrangement brush includes brush pieces arranged at random with a predetermined width, and the brush pieces for the microwave irradiation part 10 and the brush pieces for the microwave receiving part 11 can be arranged randomly or in a predetermined combination.

One or a plurality of rows of a circular arrangement brush refers to a brush in which the above-mentioned transverse brush is formed into a circular shape, and one row of a circular arrangement brush can be used as the microwave irradiation part 10 or the a microwave receiving part 11. In the case of a plurality of rows of a circular arrangement brush, a combination similar to that of the above-mentioned plurality of rows of a transverse brush can be used. Further, in one or a plurality of rows of a circular arrangement brush, one half of a circle can be used as the microwave irradiation part 10, and another one half thereof can be used as the microwave receiving part 11.

One or a plurality of rows of a semi-circular arrangement brush refers to a brush in which the above-mentioned transverse brush is formed into a semi-circular shape, and one row of a semi-circular arrangement brush can be used as the microwave irradiation part 10 or the microwave receiving part 11. In the case of a plurality of rows of a semi-circular arrangement brush, a combination similar to that of the above-mentioned plurality of rows of a transverse brush can be used. Further, in one or a plurality of rows of a semi-circular arrangement brush, one half of a semi-circle can be used as the microwave irradiation part 10, and another one half thereof can be used as the microwave receiving part 11.

Each unit of pieces of the brush-like structure 12 may be straight or curved. A tip end of the brush-like structure 12 may be curved in an inward direction. Further, it is preferred that tip portions of the brush-like structure 12 be aligned in a row.

The brush-like structure 12 may be a wire having elasticity connected to the central conductor 2 or the external conductor 4 directly or indirectly, or may have the longitudinal needle-like structure in which the central conductor 2 or the external conductor 4 is formed to be thin. It is only necessary that a plurality of brush pieces be collected to form a brush shape and have an elastic force capable of abrading and crushing even a relatively hard solid organ. When the tips of brush pieces are reduced in the width, a narrow groove can be formed in cerebral surgery or the like, thereby advantageously eliminating the need to crush and coagulate an organ excessively.

Further, the brush-like structure 12 is considered to be applicable as a tool (as a raspatory) for removing organs from each other while performing hemostasis between the organs at a time of a general surgical operation.

Further, each unit of the brush-like structure 12 may have a halved shape. When the coaxial structure including an insulating layer between the central conductor 2 and the external conductor 4 for performing microwave irradiation is cut in the longitudinal direction, and a plurality of extremely thin halved bodies with the central conductor 2 exposed in the longitudinal direction are arranged in a brush shape, this arrangement can be used directly as a brush.

(Electrode)

As the electrode used in the present invention, an electrode known per se can be used, and a needle-shaped electrode is preferred. One or a plurality of electrodes may be set on both the central conductor 2 and the external conductor 4, to thereby obtain a bipolar electrode. Further, one or a plurality of electrodes may be set on the central conductor 2 or the external conductor 4, to thereby obtain a unipolar electrode.

(Forceps)

As the forceps used in the present invention, forceps known per se can be used, and there may be given Kelly forceps, Kocher forceps, Pean forceps, Allis forceps, and the like. However, the forceps are not particularly limited.

Further, the tip end of the central conductor and/or the tip end of the external conductor may be formed into the shape of blades for scissors, to thereby have a function to cut a tissue.

(Scissors)

As the scissors used in the present invention, scissors known per se, in particular, surgical scissors can be used.

Further, the tip end of the central conductor and/or the tip end of the external conductor may be formed into the shape of scissors, to thereby have a function to cut a tissue.

(Knife)

The knife used in the present invention is not particularly limited as long as the knife is an endoscopic knife or a scope-assisted surgical knife.

Further, the tip end of the external conductor may be formed into the shape of an endoscopic knife or a scope-assisted surgical knife, to thereby have a function of a knife.

(Application of Microwave-irradiating Instrument of Present Invention)

Besides the application of related-art microwave-irradiating instrument for medical use, in particular, for surgery use, the micro-irradiating instrument of the present invention has succeeded in reduction of a diameter of the coaxial cable 6. Thus, the microwave-irradiating instrument 1 of the present invention can also be utilized for the following instruments.

(1) A medical microwave-irradiating instrument that can be inserted into an endoscope and/or a catheter.

(2) A microwave-irradiating instrument for ablation therapy.

(3) An industrial coaxial cable-shaped microwave-irradiating instrument.

(4) A coaxial cable-shaped microwave-transmitting instrument.

Now, the microwave-irradiating instrument 1 of the present invention is descried in detail byway of specific examples. However, the present invention is not limited to the examples.

EXAMPLE 1

(Microwave-irradiating Instrument of Present Invention)

Now, microwave-irradiating instruments according to first to sixth embodiments of the present invention are described.

(First Embodiment)

Figure 3:
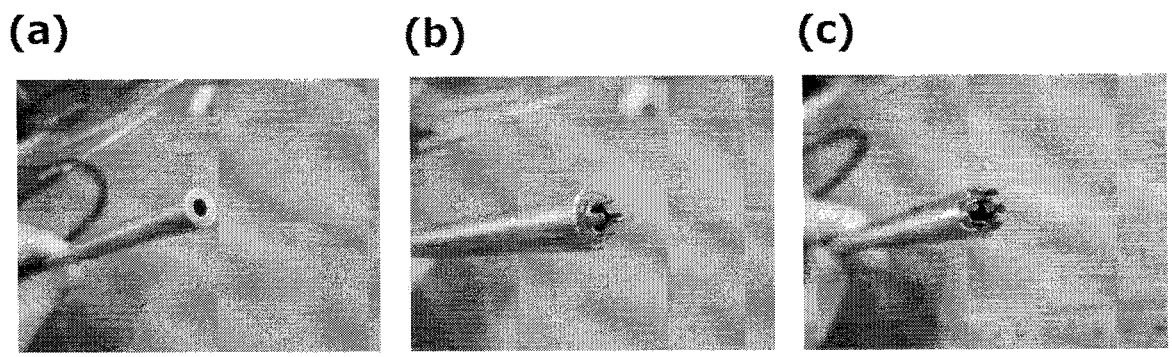
FIG. 3(a) is an illustration of a microwave-irradiating instrument according to a second embodiment of the present invention.
FIG. 3(b) is an illustration of a microwave-irradiating instrument according to a first embodiment of the present invention.
FIG. 3(c) is an illustration of a microwave-irradiating instrument 1 according to a third embodiment of the present invention.

The microwave-irradiating instrument 1 according to a first embodiment of the present invention is described with reference to FIG. 2 and FIG. 3(*b*).

In the microwave-irradiating instrument 1 according to the first embodiment of the present invention, the coaxial cable 6 includes the central conductor 2 including the channel 5, the insulator 3 configured to cover the central conductor 2, and the external conductor 4 configured to cover the insulator 3. The suction device 13 or the pump 14 is connected to the end 7 of the coaxial cable, and hence the channel 5 serves as the suction tube 8 or the supply tube 9. The brush-like structure 12 is arranged in the central conductor 2 and serves as the microwave-irradiating part 10, and the tip end of the external conductor 4 serves as the microwave-receiving part 11.

The diameter of a coaxial cable-like device portion is about 8 mm, and the length of the coaxial cable is about 17 cm.

(Second Embodiment)

The microwave-irradiating instrument 1 according to a second embodiment of the present invention is described with reference to FIG. 3(*a*).

In the microwave-irradiating instrument 1 according to the second embodiment of the present invention, the coaxial cable 6 includes the central conductor 2 including the channel 5, the insulator 3 configured to cover the central conductor 2, and the external conductor 4 configured to cover the insulator 3. The suction device 13 or the pump 14 is connected to the end 7 of the coaxial cable, and hence the channel 5 serves as the suction tube 8 or the supply tube 9. The tip end of the central conductor 2 serves as the microwave-irradiating part 10, and the tip end of the external conductor 4 serves as the microwave-receiving part 11.

The diameter of a coaxial cable-like device portion is about 8 mm, and the length of the coaxial cable is about 17 cm.

(Third Embodiment)

The microwave-irradiating instrument 1 according to a third embodiment of the present invention is described with reference to FIG. 3(*c*).

In the microwave-irradiating instrument 1 according to the third embodiment of the present invention, the coaxial cable 6 includes the central conductor 2 including the channel 5, the insulator 3 configured to cover the central conductor 2, and the external conductor 4 configured to cover the insulator 3. The suction device 13 or the pump 14 is connected to the end 7 of the coaxial cable, and hence the channel 5 serves as the suction tube 8 or the supply tube 9. The brush-like structure 12 is arranged in the central conductor 2 and serves as the microwave-irradiating part 10. The brush-like structure 12 is arranged in the external conductor 4 and serves as the microwave-receiving part 11.

The diameter of a coaxial cable-like device portion is about 8 mm, and the length of the coaxial cable is about 17 cm.

(Fourth Embodiment)

Figure 8:
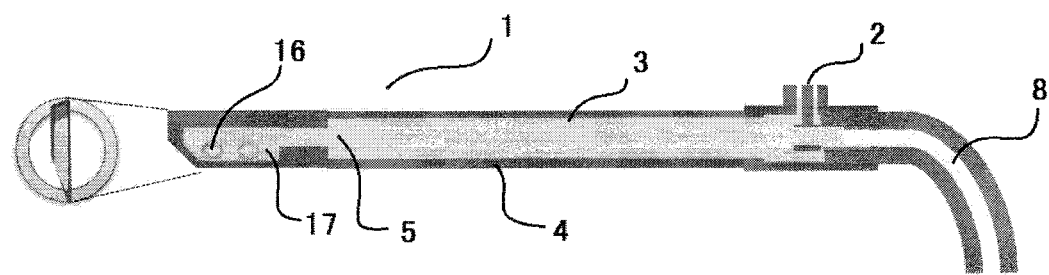
FIG. 8 is an illustration of a microwave-irradiating instrument according to a fourth embodiment of the present invention.

The microwave-irradiating instrument 1 according to a fourth embodiment of the present invention is described with reference to FIG. 8.

In the microwave-irradiating instrument 1 according to the fourth embodiment of the present invention, the coaxial cable 6 includes the central conductor 2 including the channel 5, the insulator 3 configured to cover the central conductor 2, and the external conductor 4 configured to cover the insulator 3.

The microwave-receiving part 11 is located at the tip end of the external conductor 4 and has a shape of a knife 17. Further, the microwave-irradiating part 10 is also located at the tip end of the central conductor 2 and has a shape of a knife 17, as needed.

With this, the microwave-irradiating instrument 1 of the present invention enables resection of a tissue while irradiating a microwave to the tissue.

Further, the knife can also be directly or indirectly connected to the tip ends of the central conductor 2, the insulator 3, and/or the external conductor 4. When the knife is connected to the central conductor 2, a microwave can be radiated from the knife.

(Fifth Embodiment)

Figure 9:
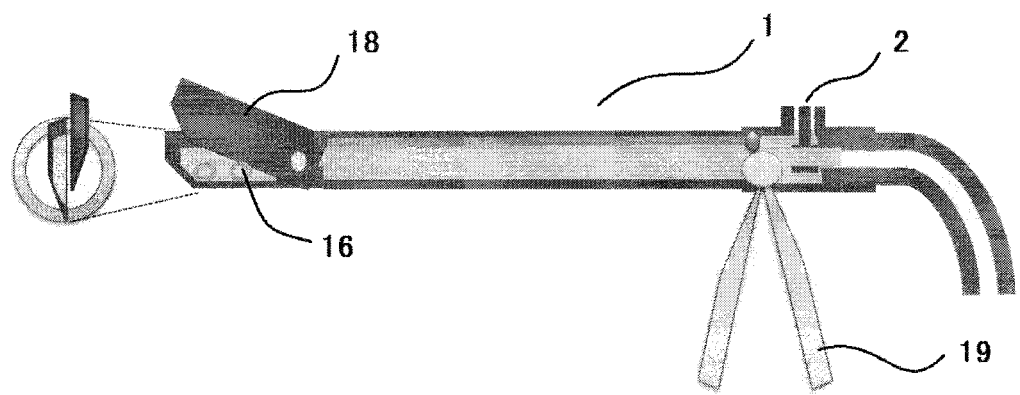
FIG. 9 is an illustration of a microwave-irradiating instrument according to a fifth embodiment of the present invention.

The microwave-irradiating instrument 1 according to a fifth embodiment of the present invention is described with reference to FIG. 9.

In the microwave-irradiating instrument 1 according to the fifth embodiment of the present invention, the coaxial cable 6 includes the central conductor 2 including the channel 5, the insulator 3 configured to cover the central conductor 2, and the external conductor 4 configured to cover the insulator 3.

Two blades of scissors-shaped forceps 18 serve as the microwave-irradiating part 10 and the microwave-receiving part 11, respectively, and a microwave can be applied and received between the two blades. Further, a lever 19 is arranged on the microwave-irradiating instrument 1 so that the operation of the forceps can be controlled.

With this, the microwave-irradiating instrument 1 of the present invention enables resection of a tissue while irradiating (after irradiating) a microwave to the tissue with a microwave.

Further, when the microwave-irradiating part 10 is located at the tip end of the central conductor 2 and has a shape of blades for forceps, and the microwave-receiving part 11 is located at the tip end of the external conductor 4 and has a shape of blades for forceps, a microwave can be applied and received between the two blades.

(Sixth Embodiment)

Figure 10:
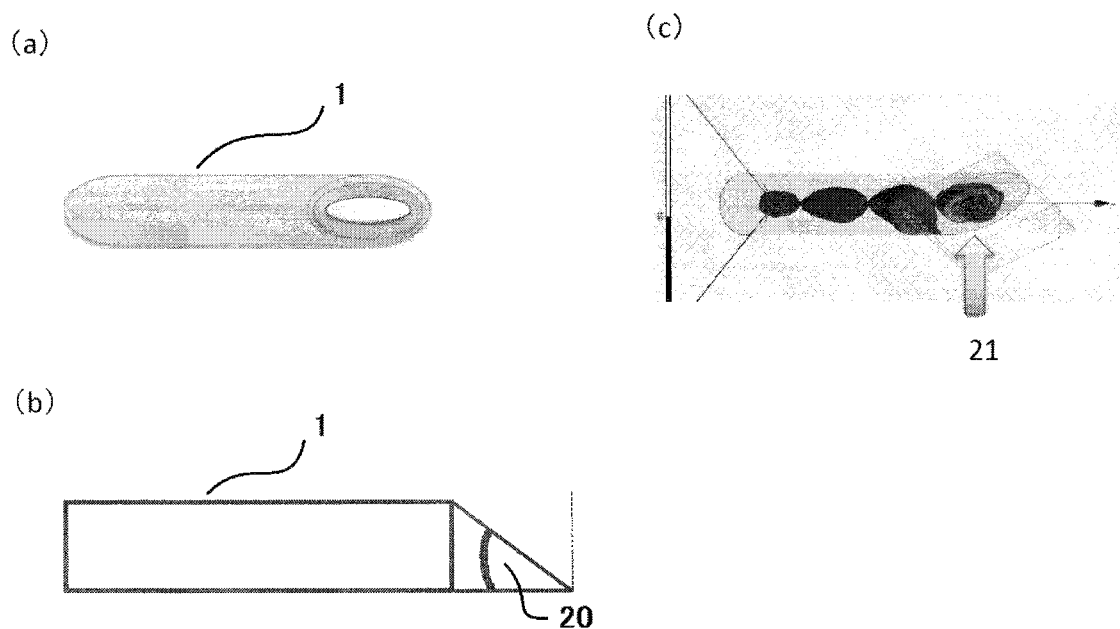
FIG. 10(a) is an illustration of a microwave-irradiating instrument according to a sixth embodiment of the present invention.
FIG. 10(b) is a sectional shape view of the microwave-irradiating instrument according to the sixth embodiment in a long axis direction.
FIG. 10(c) is an illustration of microwave irradiation simulation results of the microwave-irradiating instrument according to the sixth embodiment.

The microwave-irradiating instrument 1 according to a sixth embodiment of the present invention is described with reference to FIG. 10.

In the sixth embodiment, the tip end (microwave irradiation direction) of the microwave-irradiating instrument 1 is cut at an angle so that an inner angle (angle 20 of the tip end portion) with respect to a surface vertical to the long axis direction of the microwave-irradiating instrument 1 falls within a range of from 10° to 60° (see FIG. 10(a) and FIG. 10(b)).

It is verified that a microwave can be radiated to a tissue efficiently with the shape of the tip end (see FIG. 10(c)).

EXAMPLE 2

(Verification of Microwave Irradiation Through Use of Microwave-irradiating Instrument of Present Invention)

Microwave irradiation was verified through use of the microwave-irradiating instrument of the present invention. Specifically, a liver of a beagle dog was subjected to microwave irradiation through use of the microwave-irradiating instrument 1 (medical microwave-irradiating instrument 1) according to the first and second embodiments.

Figure 4:
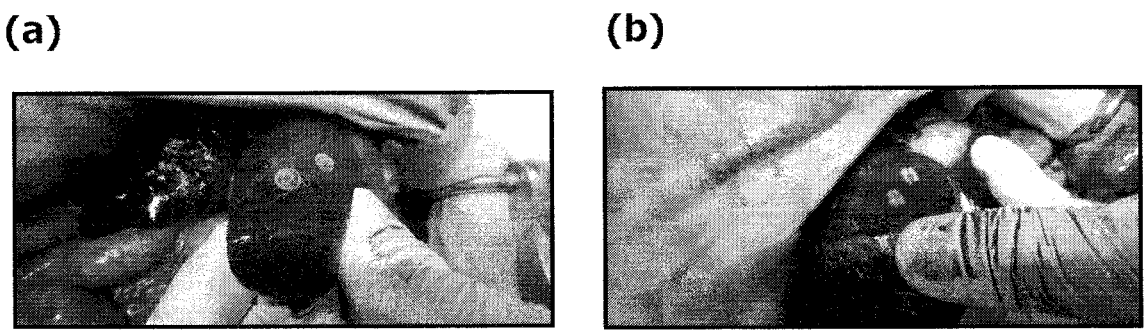
FIG. 4 (a) is an illustration of microwave irradiation results obtained by using the microwave-irradiating instrument according to the first embodiment.

The verification results of microwave irradiation through use of the microwave irradiation instrument 1 according to the second embodiment are illustrated in FIG. 4(a). As is apparent from FIG. 4(a), the microwave-irradiating instrument 1 according to the second embodiment was able to accurately irradiate a microwave to an assumed affected area.

The verification results of microwave irradiation through use of the medical microwave irradiation instrument 1 according to the first embodiment are illustrated in FIG. 4(b). As is apparent from FIG. 4(b), the medical microwave-irradiating instrument 1 according to the first embodiment was able to accurately irradiate a microwave to an assumed affected area.

Besides the effect of the medical microwave-irradiating instrument 1 of the present invention of being capable of accurately irradiating a microwave to the affected area as described above, the following effects were verified separately.

(1) The medical microwave-irradiating instrument 1 according to the fourth embodiment can simultaneously irradiate a microwave to a tissue while enabling cutting of the tissue (affected area) with a knife, and further can suck a cut piece of the tissue through the channel 5.

(2) The medical microwave-irradiating instrument 1 according to the fifth embodiment can simultaneously irradiate a microwave to a tissue while cutting (pinching) the tissue (affected area) with forceps, and further can suck a cut piece of the tissue through the channel 5.

(3) When the medical microwave-irradiating instrument 1 has the soft channel structure having a length of from 30 cm to 300 cm, an outer diameter of from 1 mm to 30 mm, and an inner diameter of from 0.5 mm to 25 mm, the medical microwave-irradiating instrument 1 can be inserted through a hole of endoscopic forceps, to thereby subject a tissue to hemostasis and fracture, suck a body fluid such as blood, and spray a liquid such as saline. Alternatively, the medical microwave-irradiating instrument 1 can be inserted alone into a body cavity, to thereby subject a tissue to hemostasis and fracture, suck a body fluid such as blood, and spray a liquid such as saline.

(4) Due to the microwave-irradiating part 10 in which the brush-like structure 12 (brush-like protrusion) is arranged in the central conductor 2, a microwave can be transmitted from the tip end of the protrusion to the external conductor 4. With this, a microwave can be radiated with the tip end held in direct contact with a tissue (affected area), and hence coagulation and hemostasis can easily be performed. Further, the tissue can also easily be abraded by moving the brush-like structure 12.

(5) The channel 5 serves as the suction tube 8 and the supply tube 9, and hence washing of a tissue in the periphery of a coagulated tissue and suction of the coagulated tissue and blood can be performed simultaneously with the above-mentioned coagulation and hemostasis. That is, an operator can significantly omit the operation for washing and suction of the tissue in the periphery of the coagulated tissue, and a burden is not given to a patient.

(6) A suction tube and a supply tube of the related-art microwave-irradiating instrument are arranged at positions away from a microwave-irradiating part. That is, when a microwave is irradiated to a tissue through use of the related-art microwave-irradiating instrument, it is necessary to move the tip end of the suction tube to the tissue and further suck a broken piece of the tissue. However, in the medical microwave-irradiating instrument 1 of the present invention, the suction tube 8 and the supply tube 9 are present on an inner diameter of the microwave-irradiating part 10. Thus, when a microwave is irradiated to a tissue, a broken piece of the tissue can easily be sucked without moving the tip end of the suction tube 8 to the tissue. Thus, the suction efficiency is high. Further, the tissue can be washed without moving the tip end of the supply tube 9 to the tissue, and hence the washing efficiency is also high.

(7) The suction tube and the supply tube of the related-art microwave-irradiating surgical instrument are arranged separately from the microwave-irradiating part. That is, when a microwave is irradiated to a tissue through use of the related-art microwave-irradiating instrument, the presence of the tip end of the suction tube and the tip end of the supply tube narrows the field of view of an operator. However, in the medical microwave-irradiating instrument 1 of the present invention, the suction tube 8 and the supply tube 9 are present on an inner diameter of the microwave-irradiating part 10, and hence the field of view of the operator is not narrowed.

Specifically, the medical microwave-irradiating instrument 1 of the present invention has succeeded in extreme reduction in size as compared to the related-art microwave-irradiating instrument. In addition, the medical microwave-irradiating instrument 1 of the present invention enables easy operation of coagulation, hemostasis, washing, and suction of a tissue, and further enables those operations to be performed efficiently within a short period of time.

The microwave-irradiating instrument of the present invention also has the following effects as well as the above-mentioned effects.

(8) When a transmission cable is introduced into the channel 5, signal information of a microwave irradiation target can be acquired. In particular, when a transmission cable including a camera at a tip end is introduced into the channel 5, an image of the microwave irradiation target can be acquired.

(9) When a direct current supply device is introduced into the channel 5, a direct current can be supplied to a microwave irradiation target, and further a change in a direct current electric resistance value (preferably, the direct current electric resistance value reaches 0) is measured. Thus, the completion of coagulation of a tissue can be detected.

(10) When a high-frequency wave supply device is introduced into the channel 5, a high-frequency wave can be supplied to a microwave irradiation target, and hemostasis enhancement can be performed.

(11) When an ultrasonic wave supply device is introduced into the channel 5, an ultrasonic wave can be supplied to a microwave irradiation target, thereby being capable of assisting an operation of burning out and cutting a tissue.

(12) When a light supply device is introduced into the channel 5, light can be supplied to a microwave irradiation target, and hence a surgical field can be illuminated.

INDUSTRIAL APPLICABILITY

The medical microwave-irradiating instrument of the present invention has succeeded in extreme reduction in size unlike the related-art microwave-irradiating surgery instrument. Further, the medical microwave-irradiating instrument enables a device tip end portion to sufficiently radiate a microwave in various sensitive treatments required for surgery, and enables local coagulation, immobilization, hemostasis, and sealing of a fine living tissue efficiently within a short period of time. Further, the medical microwave-irradiating instrument of the present invention enables treatment to be performed with small power, and thus the safety thereof is high.

Thus, the medical microwave-irradiating instrument of the present invention is remarkably excellent in safety and operability in scope-assisted therapy in a surgical treatment area in a medical field, in particular, a cerebral surgery area, an intravascular surgery area, and gastroenterological medicine.

In addition, the microwave-irradiating instrument of the present invention can also be used as an industrial coaxial cable.

REFERENCE SIGNS LIST

1: microwave-irradiating instrument
2: central conductor
3: insulator
4: external conductor
5: channel
6: coaxial cable
7: end of coaxial cable
8: suction tube
9: supply tube
10: microwave-irradiating part
11: microwave-receiving part
12: brush-like structure
13: suction device
14: pump
15: connector
16: small hole
17: shape of knife
18: forceps
19: lever
20: angle of tip end portion
21: microwave-irradiating area

The invention claimed is:
1. A microwave-irradiating instrument, comprising:
(1) a central conductor having a portion that has a hollow shape;
(2) a contiguous channel, which passes through the portion that has the hollow shape;
(3) an insulator configured to cover a part or an entirety of the central conductor;
(4) an external conductor configured to cover a part or an entirety of the insulator;
(5) a microwave-irradiating part directly or indirectly connected to the central conductor or the external conductor; and
(6) a microwave-receiving part is directly or indirectly connected to the external conductor when the microwave-irradiating part is directly or indirectly connected to the central conductor or the microwave-receiving part is directly or indirectly connected to the central conductor when the microwave-irradiating part is directly or indirectly connected to the external conductor, wherein the contiguous channel includes a suction tube, a supply tube, and a connector for connection to a microwave oscillator, and wherein the contiguous channel is capable of simultaneously performing a function of transmitting a microwave and functions of the suction tube and the supply tube.

2. The microwave-irradiating instrument according to claim 1, wherein the contiguous channel enables a liquid and/or air to pass through the channel.

3. The microwave-irradiating instrument according to claim 1, wherein the contiguous channel includes a transmission cable, which includes a camera at a tip end of the transmission cable, to enable acquisition of an image of a microwave irradiation target.

4. The microwave-irradiating instrument according to claim 1, wherein the contiguous channel includes an energy supply conductive wire and/or instrument, which is or are configured to supply energy other than microwave energy, to enable irradiation of an energy other than microwave energy to a microwave irradiation target.

5. The microwave-irradiating instrument according to claim 4, wherein the energy supply conductive wire and/or instrument has a hollow structure.

6. The microwave-irradiating instrument according to claim 1, wherein the contiguous channel includes a temperature and/or electric resistance measurement sensor to enable measurement of a temperature and/or an electric resistance value of a microwave irradiation target.

7. The microwave-irradiating instrument according to claim 1, wherein the contiguous channel includes a vibration function instrument to enable vibration of a microwave irradiation target.

8. The microwave-irradiating instrument according to claim 1, wherein the portion of the central conductor surrounds a part of the contiguous channel.

9. The microwave-irradiating instrument according to claim 1, wherein the microwave-irradiating instrument comprises a coaxial cable.

10. The microwave-irradiating instrument according to claim 1, wherein the microwave-irradiating instrument comprises a coaxial cable-shaped microwave transmission instrument.

11. The microwave-irradiating instrument according to claim 1, wherein the microwave-irradiating instrument comprises a medical microwave-irradiating instrument.

12. The microwave-irradiating instrument according to claim 1, wherein a combination of the microwave-irradiating part and the microwave receiving part is any one of the combinations comprising:

(1) the microwave-irradiating part directly or indirectly connected to the central conductor includes a brush-like structure, and the microwave-receiving part directly or indirectly connected to the external conductor includes the brush-like structure;

(2) the microwave-irradiating part directly or indirectly connected to the central conductor is located at a tip end of the central conductor, and the microwave-receiving part directly or indirectly connected to the external conductor is located at a tip end of the external conductor; and (3) the microwave-irradiating part directly or indirectly connected to the central conductor includes a brush-like structure, and the microwave-receiving part directly or indirectly connected to the external conductor is located at the tip end of the external conductor.

\* \* \* \* \*